(12) United States Patent
Brask (10) Patent No.: US 11,475,992 B2
(45) Date of Patent: Oct. 18, 2022

(54) SYSTEM AND METHOD OF SYNCHRONIZING MEDICAL DEVICE DATABASES

(71) Applicant: Fenwal, Inc., Lake Zurich, IL (US)

(72) Inventor: David Brask, Mundelein, IL (US)

(73) Assignee: Fenwal, Inc., Lake Zurich, IL (US)

( * ) Notice: Subject to any disclaimer, the term of this patent is extended or adjusted under 35 U.S.C. 154(b) by 42 days.

(21) Appl. No.: 16/021,466

(22) Filed: Jun. 28, 2018

(65) Prior Publication Data

US 2019/0006044 A1 Jan. 3, 2019

Related U.S. Application Data

(60) Provisional application No. 62/526,161, filed on Jun. 28, 2017.

(51) Int. Cl.
*G16H 40/20* (2018.01)
*G16H 40/60* (2018.01)
(Continued)

(52) U.S. Cl.
CPC ............ *G16H 40/20* (2018.01); *G16H 40/40* (2018.01); *G16H 40/60* (2018.01); *A61B 5/0022* (2013.01); *G16H 10/60* (2018.01)

(58) Field of Classification Search
CPC . G06F 8/24; G06F 16/24; G06F 16/40; G06F 19/00; G06F 19/34; G06Q 10/06;
(Continued)

(56) References Cited

U.S. PATENT DOCUMENTS 8,065,161 B2 * 11/2011 Howard ................ A61M 5/142
705/2
9,122,716 B1 * 9/2015 Naganathan ............ G06F 16/27
(Continued)

FOREIGN PATENT DOCUMENTS

EP 1647908 A2 * 4/2006 ....... G06F 16/24552
EP 1647908 A2 4/2006
(Continued)

OTHER PUBLICATIONS

Extended European Search Report for counterpart EP Application No. 18179029 (dated Nov. 9, 2018) (9 pages).

*Primary Examiner* — Christopher L Gilligan
*Assistant Examiner* — Chance L Smith
(74) *Attorney, Agent, or Firm* — Cook Alex Ltd.

(57) ABSTRACT

A medical device data management system comprising a server for updating data relating to medical devices, comprising a first database comprising a first plurality of data objects, wherein the first database is in communication with an interface via an interface application. The system comprises a second database comprising a second plurality of data objects containing an analogue of the data objects from the first plurality, wherein the second database is in communication with a plurality of medical devices via a medical device application. The system also comprises a synchronization application in communication with the first and second databases, and the synchronization application is configured to receive a notification when a data object from the first plurality changes in value, identify within the second plurality target analogues of the data object from the first plurality, and replace the target analogues with changed values of the data object from the first plurality.

9 Claims, 3 Drawing Sheets

(51) Int. Cl.
*G16H 40/40* (2018.01)
*G16H 10/60* (2018.01)
*A61B 5/00* (2006.01)

(58) Field of Classification Search
CPC ........ G06Q 10/10; G06Q 10/60; G06Q 50/22; G06Q 50/24; G16H 10/60; G16H 40/20; G16H 40/40; G16H 40/63; G16H 40/60; H04W 56/00; A61B 5/0022
See application file for complete search history.

(56) References Cited

U.S. PATENT DOCUMENTS

| | | | | |
|---|---|---|---|---|
| 2004/0167804 | A1* | 8/2004 | Simpson | A61B 5/0002 705/3 |
| 2005/0144043 | A1* | 6/2005 | Holland | G06F 19/326 705/3 |
| 2005/0278194 | A1* | 12/2005 | Holland | G06F 19/3418 705/2 |
| 2006/0089544 | A1* | 4/2006 | Williams | G16H 40/63 600/300 |
| 2007/0094308 | A1* | 4/2007 | Mitchell | G06F 16/27 |
| 2009/0112915 | A1* | 4/2009 | Lele | G06F 9/4488 |
| 2009/0156991 | A1* | 6/2009 | Roberts | G06Q 50/22 604/67 |
| 2010/0049542 | A1 | 2/2010 | Benjamin et al. | |
| 2013/0179186 | A1* | 7/2013 | Birtwhistle | G16H 10/60 705/3 |
| 2014/0025392 | A1* | 1/2014 | Chandrasenan | G06F 19/3481 705/2 |
| 2014/0350966 | A1* | 11/2014 | Khatana | G16H 10/60 705/3 |
| 2016/0012184 | A1* | 1/2016 | Nimmagadda | G06F 16/25 705/3 |
| 2016/0344808 | A1* | 11/2016 | Smith | H04L 67/12 |
| 2017/0196457 | A1* | 7/2017 | Thakur | A61B 5/0031 |
| 2018/0144817 | A1* | 5/2018 | Lofgren | A61M 5/14 |

FOREIGN PATENT DOCUMENTS

| | | |
|---|---|---|
| WO | 2004010319 A2 | 1/2004 |
| WO | 2004107162 A1 | 12/2004 |

* cited by examiner

SYSTEM AND METHOD OF SYNCHRONIZING MEDICAL DEVICE DATABASES

CROSS-REFERENCE TO RELATED APPLICATIONS

This application claims the benefit of U.S. Provisional Patent App. No. 62/526,161 filed Jun. 28, 2017, which is expressly incorporated herein by reference in its entirety.

FIELD OF THE DISCLOSURE

The present disclosure is directed to data replication and/or data synchronization. More specifically, the present disclosure relates to methods, systems, and apparatus to facilitate data reconciliation and/or data synchronization for medical devices.

BACKGROUND

Medical devices are used for blood collection, apheresis, biological fluid processing, therapeutics, drug infusion, medical laboratory devices, etc. For example, infusion pumps are used in the field of medicine to administer drugs to patients often over an extended time period. Sophistication in medical devices has increased as availability of drugs, therapeutic techniques, and technological capabilities have improved. Achieving this sophistication and maintaining ease of use have become more important for medical device manufacturers.

For example, infusion pumps are used to administer drugs and other medicaments often in a clinical setting. An infusion pump may provide a controlled amount of the medicament over time to the patient. The amount may be administered pursuant to parameters entered, for example, by a clinician into the pump using a pump user interface.

To avoid errors in drug administration, some infusion pumps may hold a library of drug names and associated parameters, e.g., rate of infusion, frequency of infusion, etc. The drug library may be created and/or updated by a health care professional and/or health center employee. In some cases, overriding or reprogramming of parameters programmed into the drug library may be desired. Similarly, apheresis devices may hold a library of fluid procedures and associated parameters, e.g., type of procedure, patient parameters, rate of transfusion, volume of collection, etc. The library for apheresis devices and other biological fluid processing devices may be updated and controlled by a health care professional.

SUMMARY

According to an exemplary embodiment, the present disclosure is directed to a medical device data management system comprising a server computer for updating data relating to a plurality of medical devices, comprising a first database comprising a first plurality of data objects, wherein the first database is in communication with one or more external interfaces via an interface application. The system also comprises a second database comprising a second plurality of data objects containing one or more analogues of the data objects from the first plurality, wherein the second database is in communication with a plurality of medical devices via a medical device application. The system also comprises a synchronization application in communication with the first and second databases, and the synchronization application is configured to receive a notification when a data object or set of data objects from the first plurality changes in value, identify within the second plurality target analogues of the data object or the set of data objects from the first plurality, and replace the target analogues with changed values of the data object or the set of data objects from the first plurality.

According to an exemplary embodiment, the present disclosure is directed to a computer-implemented medical device management method for updating data relating to a plurality of medical devices, said method comprising providing a first database comprising a first plurality of data objects and a second database comprising a second plurality of data objects, wherein the first and second pluralities contain one or more analogues of data objects. The method also comprises notifying a synchronization application when a data object or set of data objects from the first or second database changes in value, wherein a notification identifies an origination database and one or more destination databases. The method also comprises identifying target analogues of the data object or the set of data objects within the one or more destination databases and replacing the target analogues with changed values of the data object or the set of data objects.

According to an exemplary embodiment, the present disclosure is directed to a computer-implemented medical device management system comprising a first database comprising a first plurality of data objects and a second database comprising a second plurality of data objects, wherein the first and second pluralities contain one or more analogues of data objects. The system also comprises a synchronization application configured to receive notifications when a data object or set of data objects from the first or second database changes in value, wherein a notification identifies an origination database, one or more destination databases, and updated data objects or set of updated data objects. The system also comprises coded instructions of the synchronization application containing rules and conditions for identifying and updating target analogues within the one or more destination databases based on destination database values and data object type values. The synchronization application is configured to update target analogues in the destination databases that meet the rules and conditions.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The following discloses example methods, apparatus, systems, and articles of manufacture including, among other components, firmware and/or software executed on hardware. It should be noted that such methods, apparatus, systems and articles of manufacture are illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

Some embodiments may allow for efficient replication of data objects, databases, and/or data sets from one system and/or database to another while minimizing performance disruption to the overall system.

Some embodiments may facilitate management of medical devices including blood collection or apheresis devices, infusion pumps, drug delivery pumps, and/or other medical devices. For example, an infusion pump may infuse fluids, medication, or nutrients into a patient. An infusion pump may be used intravenously, subcutaneously, arterially, and/or epidurally, for example. For example, an infusion pump may administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) may provide input regarding type of infusion, mode, and/or other device parameter. For example, continuous infusion may provide small pulses of infusion (e.g., between 500 nanoliters and 10 milliliters), with a pulse rate based on a programmed infusion speed. Intermittent infusion may alternate between a high infusion rate and a low infusion rate with timing programmable to keep a cannula open, for example. Patient-controlled infusion may provide on-demand infusion with a preprogrammed ceiling to avoid patient intoxication. The infusion rate may be controlled by a pressure pad or button that can be activated by the patient, for example. Infusion pumps may include large volume pumps (e.g., for nutrient solution delivery to feed a patient), small-volume pumps (e.g., for medicine delivery), etc.

In some embodiments, an operator or administrator may configure a medical device, such as an infusion pump, apheresis device, etc., and/or set one or more parameters for interaction between the device and a domain controller and/or a provider data management system. Certain examples may provide efficiency in updating a dynamic data management system and allow for dynamic exchange of information between medical devices and the data management system, while maintaining system reliability and performance.

Some embodiments may facilitate synchronization of a data set updated by a medical device, such as an infusion pump, apheresis device, etc., throughout multiple databases within a data management system. Certain examples may determine a data set synchronization or update policy associated with a medical device data management system. If a data set is updated by a medical device, e.g., automatically updated or updated by a user, a synchronization policy may determine how the updated data set (e.g., derived from a new or updated drug library, etc.) may be distributed to one or more databases within the medical device data management system, even if a pre-existing data set is associated with the medical device(s) subject to the updated data set.

A data management system may interact with medical devices for flexible, remote configuration and operation while helping to ensure data and configuration reliability and efficiency, for example. An example of a data management system is described in greater detail in U.S. Patent Publication No. 2010/0049542, the contents of which are incorporated by reference herein in its entirety. Medical device operation and data set synchronization/update may be performed simultaneously.

In certain examples, a data set may define an instruction set and/or drug settings for a medical device such as a "smart" infusion pump, apheresis device, blood collection device, etc. For example, "smart" infusion pumps may utilize a drug library and/or dose error reduction software to perform functions that assist healthcare providers with programming and calculating drug dose and delivery rates. The drug library may be a database and/or software that stores drug dosing information, blood procedure information, including dosing limits, concentration, infusion parameters, transfusion parameters, patient parameters, and drug specific advisories, for example. A drug library may generate instructions to create a suitable data set and may help reduce or prevent medication errors and associated patient harm, for example. A data set generated by a drug library may be distributed to medical devices by downloading directly at the medical device or remotely over a network, e.g., from a data management system to multiple medical devices, etc. Medical devices and/or a user connected to the data management system may also send information to the data management system and/or drug library to modify data and/or update history.

In some examples, drug libraries may let clinicians select medications and fluids from preloaded lists, which may be tailored to a healthcare facility, patient care area, etc. For example, a drug library profile used in an intensive care unit (ICU) may include vasoactive medications, but a drug library for a surgical unit may not include such medication. Some facilities may also integrate smart infusion devices with electronic medical records, computerized order entry systems, and/or medication barcode scanning systems. Integrating these systems with smart pumps may provide additional safety checks that may make administering medications safer. Healthcare facilities may choose to implement limitations, commonly called hard and soft limits (also referred to as dosing limits), on preselected drugs via the drug library. The limits set lower and upper bounds on dosage, infusion rate, etc., as defined by hospital, health system, clinic, etc. Infusion pumps and/or other devices may generate usage reports regarding how the pumps have been used, which drugs have been administered (e.g., type, frequency, dosage, total quantity, etc.), dose overrides, etc.

Figure 1:
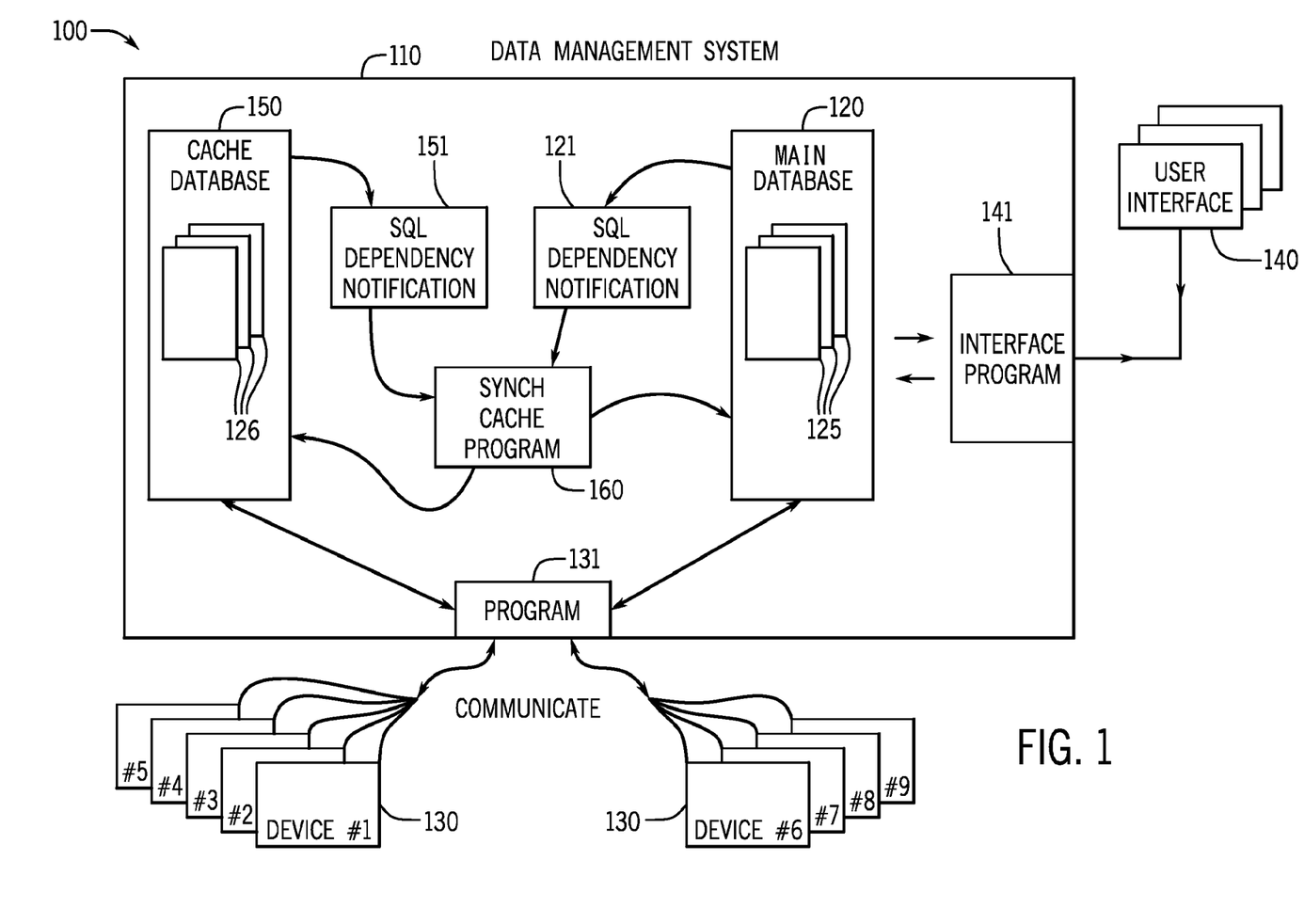
FIG. 1 is a schematic diagram of a medical device management system, according to an exemplary embodiment.

Turning to FIG. 1, an example medical device management system 100 is shown. A data management system 110 may comprise a main database 120 containing a plurality of data sets 125. The data management system 110 may be in communication with a user interface 140, e.g., web browser, computer application, mobile application, a medical device, etc., that provides an interface for an authorized user to control and/or revise contents of the data sets 125 and/or main database 120 via an application or program 141 that mediates control and modification of the main database 120 from the interface 140.

The data management system 110 may eventually distribute certain data derived from data sets 125 to one or more target medical devices 130 (e.g., pump(s), apheresis device(s), etc.) according to one or more distribution policies. The data management system 110 may also collect data from one or more target medical devices 130, such as data related to device security and authentication certificates, medical device usage history, information on drugs administered, usage history, manual overrides, etc. Exchange of data between the data management system 110 and the target medical devices 130 may be mediated by an application or program 131 that executes the data exchange between system 110 and devices 130.

The data management system 110 may also comprise one or more cache databases 150 that is a replica or near-replica of the main database 120. Incorporating one or more cache databases may enhance performance of the data management system 110 by directing significant traffic to the cache database 150 and limiting traffic to and from the main database 120. By reserving access to the main database 120 for only a limited number and/or type(s) of applications, e.g., application 141 that mediates data set modification by a user, and/or a limited number of priority events warranting immediate/direct communication with the main database 120, e.g., changes to patient history data, etc., bandwidth available to the main database 120 may be maximized.

In one embodiment, the data management system 110 may be configured such that application 131 that exchanges data between system 110 and devices 130 interacts primarily with the cache database 150 and interacts with the main database 120 in limited situations. The cache database may comprise data sets 126 that mirror or closely mirror data sets 125 of the main database 120. When the data management system 110 receives information from any of medical device 130, the cache database 150 may primarily store the new data in its data sets 126. Likewise, when the system 110 transmits data to target devices 130 according to its data set distribution policy(ies), the data may be distributed to the target devices 130 primarily from the data sets 126 of the cache database 150. Interactions between the main database 120 and application 131 may be reserved for specific events programmed into the system 110.

In order for the cache database 150 and main database 120 to communicate with each other and update each other's data sets with the latest information, the data management system 110 may comprise an application to execute the updates. The application may be based on a replication function that periodically polls a database to determine changes to target objects in the database since the last poll. In one embodiment, the application may poll the main database 120 periodically (e.g., at fixed and/or varying intervals) and replicate target objects, e.g., infusion parameters, procedure-specific advisories, etc., of the database 120. The application may then replace the analogous objects in the cache database 150 with the replicates from database 120. The application may also poll the cache database 150 periodically and replicate target objects, e.g., device history data, manual/automatic override incidents, etc., of the database 150. The application may then replace the analogous objects in the main database 120 with the updated replicates from database 150. One example of a replication function is MICROSOFT® SQL SERVER® replication for WINDOWS® and ORACLE® platforms.

In another embodiment, the application for synchronizing updated data may be based on a dependency function that updates objects when a notification is received. Illustrated in FIG. 2, the data management system 110 may comprise an application or program 160 configured to ascertain and update outdated datasets when the program 160 receives a notification. Notifications sent to program 160 may be triggered by updated data within the cache database 150 or main database 120. Some embodiments of an application based on a dependency function may obviate periodic polling of one or more databases. Some embodiments of an application based on a dependency function may also allow for updates to be made selectively to objects that have been changed. Two examples of dependency functions are SqlDependency for the .NET platform and SqlCacheDependency for the ASP.NET platform.

Figure 2:
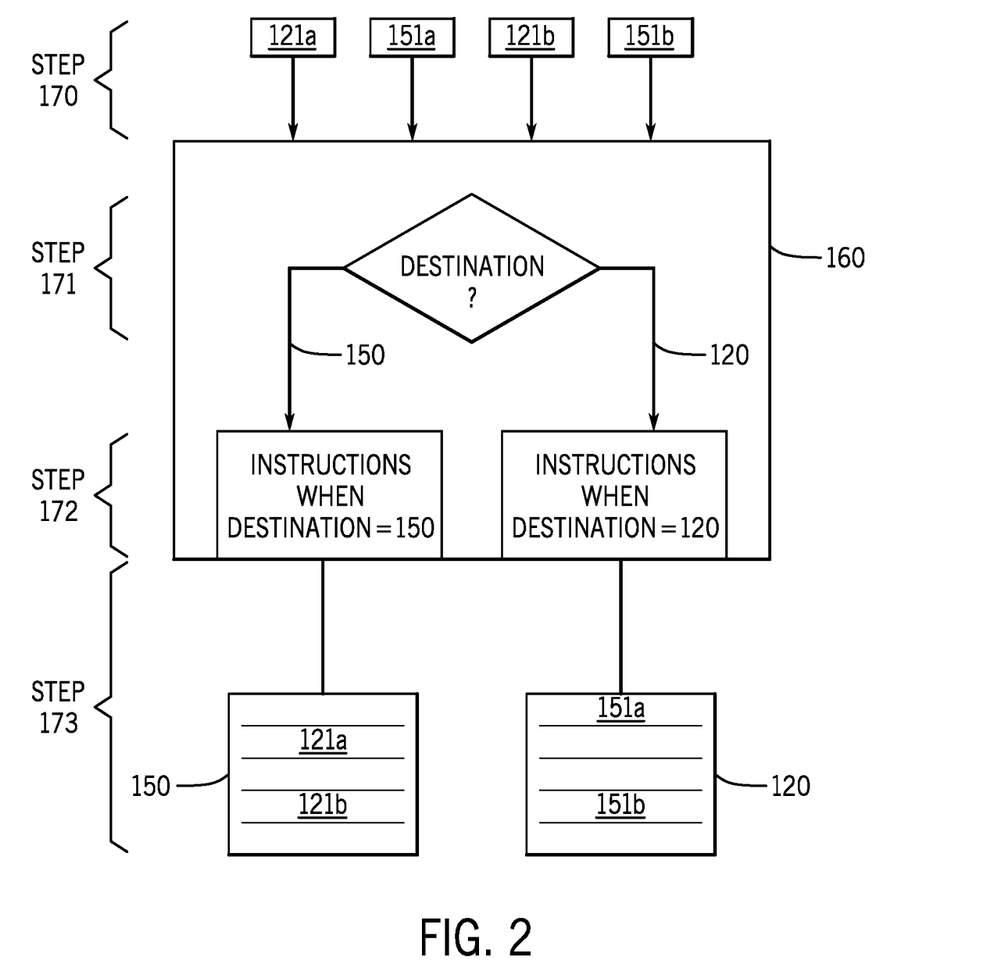
FIG. 2 is a process flow diagram illustrating a logic by which a synchronization program implements updates, according to an exemplary embodiment.

The data management system 110 may be configured to trigger and send a notification, e.g., SqlDependency notification, to application 160 when specified objects in the cache database 150 and/or main database 120 are changed, i.e., when one or more rules and/or conditions are met. For example, program 160 may be configured to receive a dependency notification 151 when a specified object and/or object type within a data set 126, e.g., relating to device usage history, etc., is updated, e.g., by data transmitted from device 130 to database 150. Application 160 may be configured to update the analogous object and/or object type in the destination database (in this example, database 120) in response to receipt of dependency notification 151. Likewise, program 160 may be configured to receive a dependency notification 121 when a specified object(s) and/or object type(s) within a data set(s) 125, e.g., relating to new dosing limitations, etc., is updated, e.g., by data transmitted from a user at a user interface 140 to database 120. Application 160 may be configured to update the analogous object(s) and/or object type(s) in the destination database (in this example, database 150) in response to receipt of dependency notification 121 triggered by a change in the origination database (in this example, database 120). In one embodiment, multiple dependency notifications 151, 121 may be configured for various objects, object types, and/or data sets. In another embodiment, a single dependency notification 151 or 121 may be specified to be triggered by a change to any of several objects, object types, and/or data sets. In another embodiment, a dependency notification 151, 121 may be configured to be triggered by any change to an object, object type, and/or data set, except specific exceptions.

Referring to FIG. 2, a process flow diagram illustrating a logic by which the synchronization program 160 may implement updates is shown, according to an exemplary embodiment. At step 170, dependency notifications 121a and 121b triggered by changes to one or more objects in the main database 120 and dependency notifications 151a and 151b triggered by changes to one or more objects in the cache database 150 may be received by the synchronization program 160. Notifications 121a, 121b, 151a, and 151b may occur simultaneously or at different times. In one embodiment, program 160 may process notifications in the order in which they are received. At step 171, the synchronization program 160 may assign a destination to each object identified by notifications 121*a*, 121*b*, 151*a*, and 151*b*, based on information from the notifications on whether the notification was triggered by a change to main database 120 or cache database 150. At step 172, based on destination value of each object, the program 160 may check whether any of the objects are subject to any instructions coded into the program 160. For example, program 160 may be configured such that an object destined for the cache database 150 originating from the main database 120 is instructed to overwrite its analogue in the cache database 150 except when the object contains data related to usage history of a device 130 (FIG. 1), or when the object is part of, e.g., a code table, that does not benefit from frequent synchronization. In another example, program 160 may be configured such that an object destined for the main database 120 originating from the cache database 150 is instructed to overwrite its analogue in the main database 120 when the object is related to manual overrides of a device 130, except when the object is also related to drug dosing limits. At step 173, according to the instructions at step 172, the destination databases 150, 120 may be updated.

In another embodiment, synchronization program 160 may comprise a plurality of programs (not illustrated) distinguished by a specific origination database and/or destination database. For example, one synchronization program may receive notifications triggered only by changes to the cache database 150 while another synchronization program may receive notifications triggered only by changes to the main database 120. In such an embodiment, each synchronization program may be configured with a single destination and a single set of instructions related to that destination.

Figure 3:
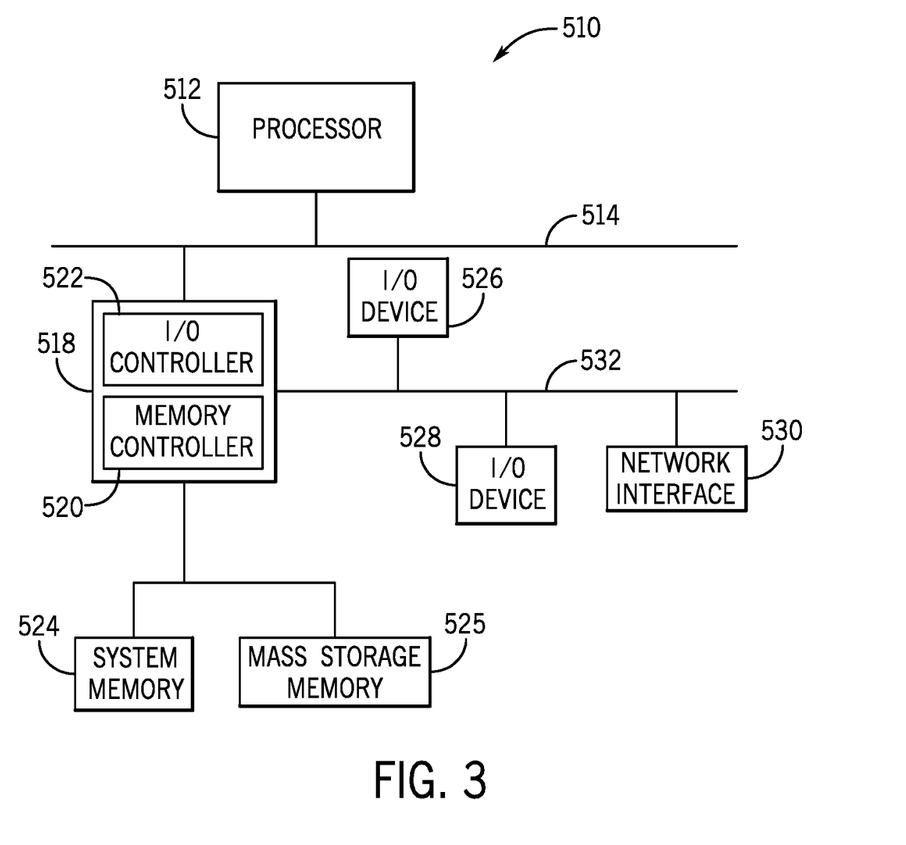
FIG. 3 is a block diagram of a data management system/server computer for processing medical device data, according to an exemplary embodiment.

FIG. 3 is a block diagram of a data management system and/or server computer for processing medical device data for presentation on a display, according to an illustrative embodiment. In alternate embodiments, the systems and methods described herein may be implemented on a single server computer, a plurality of server computers, a server farm, a cloud server environment, or using other computer resources. Data management system/server 110 and medical devices 130 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, and/or other circuit components. Data management system/server 110 and medical devices 130 may each comprise a network interface circuit configured to provide communications over one or more networks with each other and/or with other device. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of data management system/server 110. The database may be a DBMS hosted on a server host platform, such as MICROSOFT® WINDOWS XP®, MICROSOFT® WINDOWS SERVER® 2008, SQL SERVER® 2012, etc.

Referring again to FIG. 3, a block diagram of an example processor system 510 is shown that can be used to implement systems, articles of manufacture, and methods described herein. As shown in FIG. 3, the processor system 510 includes a processor 512 that is coupled to an interconnection bus 514. The processor 512 can be any suitable processor, processing unit, or microprocessor, for example. Although not shown in FIG. 3, the system 510 can be a multiprocessor system and, thus, can include one or more additional processors that are identical or similar to the processor 512 and that are communicatively coupled to the interconnection bus 514.

The processor 512 of FIG. 3 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc. that enables the processor system 510 to communicate with another processor system.

While the memory controller 520 and the I/O controller 522 are depicted in FIG. 3 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 3). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A computer-implemented medical device management method for updating data relating to a plurality of medical devices, said method comprising:
   providing a first database comprising a first plurality of data objects and a second database comprising a second plurality of data objects, wherein the first and second pluralities contain one or more analogues of data objects and the second database is a replica of the first database;
   providing a single synchronization application configured to receive notifications from both the first database and the second database,
   notifying the single synchronization application when a data object or set of data objects from the first or second database changes in value, wherein a notification identifies an origination database, one or more destination databases, and updated data objects or set of updated data objects;
   identifying target analogues of the data object or the set of data objects within the one or more destination databases based on destination database values and data object type values,
   all analogues of data objects or sets of data objects within the second database being identified as target analogues of changed values originating from the first database except when an analogous data object or set of data objects contains data related to usage history of a medical device or data that is part of a code table, and all analogues of data objects or sets of data objects within the first database being identified as target analogues of changed values originating from the second database except when an analogous data object or set of data objects contains data related to drug dosage settings or data that is part of a code table; and
   replacing the target analogues with changed values of the data object or the set of data objects, wherein
      the first database is updated by one or more external interfaces via an interface application, the one or more external interfaces allowing an authorized user to control and/or revise contents of the first database,
      the second database is configured to update and be updated directly by a plurality of medical devices via a medical device application,
      the first database communicates directly with the plurality of medical devices via the medical device application, and
      the second database does not communicate with the interface application and/or with the one or more external interfaces.

2. The method of claim 1, comprising notifying the synchronization application when changed data objects from the second database comprise information related to medical device security certificates, authentication certificates, medical device usage history, and/or manual override history.

3. The method of claim 1, wherein the notification is generated by a dependency function comprising at least one of SqlDependency and SqlCacheDependency.

4. A computer-implemented medical device management system comprising:
   a first database comprising a first plurality of data objects and a second database comprising a second plurality of data objects, wherein the first and second pluralities contain one or more analogues of data objects and the second database is a replica of the first database; and
   a single synchronization application configured to receive notifications from both the first database and the second database and to receive notifications when a data object or set of data objects from the first or second database changes in value, wherein a notification identifies an origination database, one or more destination databases, and updated data objects or set of updated data objects, with coded instructions of the synchronization application containing rules and conditions for identifying and updating target analogues within the one or more destination databases based on destination database values and data object type values, wherein
   the first database is updated by one or more external interfaces via an interface application, the one or more external interfaces allowing an authorized user to control and/or revise contents of the first database,
   the second database is configured to update and be updated directly by a plurality of medical devices via a medical device application,
   the second database does not communicate with the interface application and/or with the one or more external interfaces,
   the first database communicates directly with the plurality of medical devices via the medical device application, and
   the synchronization application is configured to identify all analogues of data objects within the second database as target analogues of changed values originating from the first database except when an analogous data object or set of data objects contains data related to usage history of a medical device or data that is part of a code table, to identify all analogues of data objects or sets of data objects within the first database as target analogues of changed values originating from the second database except when an analogous data object or set of data objects contains data related to drug dosage settings or data that is part of a code table, and to update target analogues in the destination databases that meet the rules and conditions.

5. The system of claim 4, wherein the data object or set of data objects from the second database comprise information related to medical device security certificates, authentication certificates, medical device usage history, drug dosage settings, and/or manual override history.

6. The system of claim 4, wherein the notifications are generated by a dependency function comprising at least one of SqlDependency and SqlCacheDependency.

7. The system of claim 4, wherein the first database is further configured to update and be updated by the medical device application in a limited number of programmed priority events.

8. The system of claim 4, wherein the rules and conditions comprises updating target analogues in the first database when the data object or set of data objects in the second database is changed by the medical device application, wherein the data object or set of data objects in the second database comprises at least one of device usage history, override settings, and authentication certificates.

9. The system of claim 4, wherein the rules and conditions comprises updating target analogues in the second database when the data object or set of data objects in the first database is changed by the interface application, wherein the data object or set of data objects in the first database comprises at least one of dosing limitations, device parameters, patient parameters, drug concentrations, fluid procedure settings, and drug-specific advisories.

\* \* \* \* \*